(12) United States Patent
Horn et al.

(10) Patent No.: US 6,679,855 B2
(45) Date of Patent: Jan. 20, 2004

(54) METHOD AND APPARATUS FOR THE CORRECTION OF PRESBYOPIA USING HIGH INTENSITY FOCUSED ULTRASOUND

(76) Inventors: Gerald Horn, 1150 Heather Rd., Deerfield, IL (US) 60015; Gene Zdenek, 23749 Fitzgerald St., West Hills, CA (US) 91304

( * ) Notice: Subject to any disclaimer, the term of this patent is extended or adjusted under 35 U.S.C. 154(b) by 0 days.

(21) Appl. No.: 09/870,368

(22) Filed: May 29, 2001

(65) Prior Publication Data

US 2002/0055736 A1 May 9, 2002

Related U.S. Application Data (60) Provisional application No. 60/246,906, filed on Nov. 7, 2000.

(51) Int. Cl.$^7$ .................................................. A61N 7/00
(52) U.S. Cl. .............................. 601/2; 601/3; 600/439
(58) Field of Search .......................... 601/2, 3; 600/439, 600/437

(56) References Cited

U.S. PATENT DOCUMENTS

| | | | |
|---|---|---|---|
| 4,484,569 A | * 11/1984 | Driller et al. ............ | 600/439 |
| 4,932,414 A | * 6/1990 | Coleman et al. ........... | 128/916 |
| 5,230,334 A | * 7/1993 | Klopotek ................ | 601/2 |
| 5,354,331 A | 10/1994 | Schachar | |
| 5,465,737 A | 11/1995 | Schachar | |
| 5,489,299 A | 2/1996 | Schachar | |
| 5,503,165 A | 4/1996 | Schachar | |
| 5,529,076 A | 6/1996 | Schachar | |
| 5,722,952 A | 3/1998 | Schachar | |
| 5,743,863 A | * 4/1998 | Chapelon ................ | 601/2 |
| 6,050,943 A | * 4/2000 | Slayton et al. ............. | 600/439 |
| 6,161,546 A | 12/2000 | Yavitz | |
| 6,258,082 B1 | 7/2001 | Lin | |
| 6,425,867 B1 | * 7/2002 | Vaezy et al. ............... | 600/439 |

\* cited by examiner

*Primary Examiner*—Roy D. Gibson
(74) *Attorney, Agent, or Firm*—Bell, Boyd & Lloyd LLC (57) ABSTRACT

Energy is directed at the eye in a manner so as to create discrete heating within the eye to correct vision, and in particular, to correct presbyopia. The energy is high intensity focused ultrasound (HIFU) energy directed to a specific area which when treated with the energy results in a contraction of the treated area. The contraction creates increased tension on components connected to the lens which corrects and/or prevents presbyopia.

36 Claims, 3 Drawing Sheets

METHOD AND APPARATUS FOR THE CORRECTION OF PRESBYOPIA USING HIGH INTENSITY FOCUSED ULTRASOUND

CROSS-REFERENCE

This application is a continuation-in-part application of Provisional Application Ser. No. 60/246,906, filed Nov. 7, 2000 which is incorporated herein by reference in its entirety and to which application we claim priority under 35 USC §119(e).

FIELD OF THE INVENTION

The invention relates generally to a method and device for correcting vision and more particularly to the application of laser energy or ultrasound to treat conditions such as, for example, presbyopia, hyperopia, primary open angle glaucoma and ocular hypertension.

BACKGROUND OF THE INVENTION

The ability of an eye to switch focus from a distant image to a near image depends on the ability of the eye to change its shape. Specifically, certain structures of the eye, such as, for example, the lens, must change its shape or position so that proper focus of light on the retina is achieved. A number of these structures are under muscular control.

The shape of the lens is affected by muscular action. The lens is held in place behind the iris by zonules or suspensory ligaments, which attach to the wall of the eye at the ciliary body. When the ciliary muscles contract, tension on the zonules increases, which allows the lens to increase its curvature and assume a more spheric shape because of its elastic properties.

When light from a distant visual image enters the normal emmetropic eye with a relaxed ciliary muscle, the target is in focus on the retina. However, if the eye is directed at a nearby visual target, the light is initially focused behind the retina, i.e. the image at the retina is blurred, until accommodation occurs. The image is sharpened when the lens becomes thicker with a steeper central curvature because of contraction of the ciliary muscles, resulting in a decreased diameter across the lens as well as its suspensory connections to the wall of the eye via the zonular fibers which become relaxed, allowing the lens to achieve this more spherical shape as needed.

Accommodation refers to the ability of the eye to change its focus. Accommodation is measured by the accommodative amplitude, that is, the power, measured in units called diopters (D), that the lens can vary from the non-accommodative state to a full accommodative state. For example, in accommodation for near vision, the lens increases its curvature, and as such, the amplitude of accommodation increases.

The lens continues to grow throughout an individual's lifetime. The rate of lens growth is usually about 20 to 30 microns per year. As such, the lens diameter increases over time and this increase has been correlated to a decrease in accommodative power and thus, a decrease in the ability of the lens to focus on near images. The gradual loss of accommodative power with age means that individual's ability to focus on near images declines over time. When the near point of accommodation has receded beyond a comfortable distance, the individual is said to have a condition called presbyopia.

In addition to vision impairment, conditions like presbyopia, also cause eye strain, experienced variably as fatigue, pressure behind the eye, brow ache, and generalized discomfort. To focus on an object, individuals with accommodative impairments hold objects at increasing distances from the eye. Eventually, prescription vision correction in the form of reading glasses, bifocals, trifocals, or some form of compromise between distance focus in one eye and near focus in the other, commonly known as monovision, is implemented. Typically, about 3 diopters of accommodation is necessary to read at a comfortable, close-up distance, and about 6 diopters is necessary to permit reading for extended lengths of time without premature fatigue and discomfort setting in.

Recovery of accommodative ability for conditions like presbyopia may allow an individual to have focused near vision. Preferably, such a method would be noninvasive and repeatable to allow for retreatment, should age and continued lens growth again cause an insufficient amplitude of accommodation.

Accordingly, there remains a need for a safe, effective, non-invasive method of altering the eye to correct ophthalmic conditions, such as, for example, presbyopia, where such treatment lessens or eliminates the need for auxiliary spectacle lenses and avoids the common undesirable side-effects associated with traditional eye surgery. There is also a need for an apparatus designed to practice this method.

SUMMARY OF THE INVENTION

It is an object of the invention to induce controlled cellular damage or biochemical changes to tissues that control the accommodative apparatus in order to effect biochemical changes and a healing response in a human eye that counteract the effects of presbyopia.

It is another object of the invention to increase the tension on the zonules through directly or indirectly increasing tension of surrounding tissues in a therapeutically effective amount sufficient to reverse the affects of presbyopia.

Another object of the invention is to slow the growth rate and/or stretch rate of target tissues so that the onset or progress of presbyopia is sufficiently retarded.

Another object is to alter the elasticity of the lens capsule so that the onset and progress of presbyopia is sufficiently retarded.

It is also an object of the invention to induce controlled cellular damage to target tissues to restore zonular tension so that presbyopia is sufficiently reversed to be clinically beneficial.

It is yet another object of the invention to preemptively combat presbyopia by prophylactically treating target tissues so that presbyopia may be sufficiently prevented.

These and other objects, advantages, and features of the invention will become apparent to those persons skilled in the art upon reading the details of the device and method as more fully described below. Other objects and advantages may become more apparent to those skilled in the art upon reviewing this summary of the invention, in view of the description of the preferred embodiment.

DETAILED DESCRIPTION OF PREFERRED EMBODIMENTS

Before the present methods and apparatus are described, it is to be understood that this invention is not limited to any particular embodiment described, and as such, may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a target area" includes a plurality of such areas and reference to "the step" includes reference to one or more steps and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Accommodation. The ability of the eye to change its focus from distant to near objects; process achieved by the lens changing its shape.

Amplitude of Accommodation. Amplitude of accommodation is the difference, expressed in diopters, between the far point of accommodation and the near point of accommodation measured clinically from the spectacle plane.

Facility of Accommodation. Facility of accommodation is a measure of the ease and speed of accommodative changes of the eye.

Lag of Accommodation. Lag of accommodation is the dioptric difference between the accommodative response and the stimulus to accommodation. It can be thought of as a measure of accommodative accuracy.

Accommodative Insufficiency. Accommodative insufficiency is the situation where the accommodative response is significantly less than the accommodative stimulus, leading to symptoms such as blur or asthenopia.

Accommodative Fatigue. Accommodative fatigue is the inability of the eye to adequately sustain sufficient accommodation over an extended time period.

Accommodative Infacility. Accommodative infacility is slow or difficult accommodative response to dioptric change in stimulus.

Accommodative Spasm/Excess. Accommodative spasm is a result of ciliary muscle spasm and the inability of the eye to relax accommodation.

Pseudomyopia. Pseudomyopia is an apparent refractive condition resulting from excessive accommodation caused by accommodative spasm. Patients present with typical myopic complaints such as distance blur.

Myopia. Nearsightedness; ability to see close objects more clearly than distant objects; may be corrected with glasses or contact lenses.

Hyperopia. Farsightedness; ability to see distant objects more clearly than close objects; may be corrected with glasses or contact lenses.

Latent Hyperopia. Latent hyperopia is the portion of the total hyperopia compensated for by accommodation and the tonicity of the ciliary muscle. It may be wholly or partially revealed by the use of a cycloplegic agent, but is usually not revealed by routine manifest subjective refractive procedures.

Presbyopia. The gradual loss of the eye's ability to change focus (accommodation) for seeing near objects caused by the lens becoming less elastic; associated with aging; occurs in almost all people over age 45.

Streff Syndrome (Non-Malingering Syndrome). Streff Syndrome is a condition in which there is an apparent accommodative dysfunction.

Anterior Chamber. The space in front of the iris and behind the cornea.

Aqueous Humor, Aqueous Fluid. Clear, watery fluid that flows between and nourishes the lens and the cornea; secreted by the ciliary processes.

Astigmatism. A condition in which the surface of the cornea is not spherical; causes a blurred image to be received at the retina.

Binocular Vision. The blending of the separate images seen by each eye into a single image; allows images to be seen with depth.

Blind Spot. (1) A small area of the retina where the optic nerve enters the eye; occurs normally in all eyes. (2) Any gap in the visual field corresponding to an area of the retina where no visual cells are present; associated with eye disease.

Central Retinal Artery. The blood vessel that carries blood into eye; supplies nutrition to the retina.

Central Retinal Vein. The blood vessel that carries blood from the retina.

Choroid. The layer filled with blood vessels that nourishes the retina; part of the uvea.

Ciliary Muscles. The muscles that relax the zonules to enable the lens to change shape for focusing.

Ciliary Processes. The extensions or projections of the ciliary body that secrete aqueous humor.

Cones, Cone Cells. One type of specialized light-sensitive cells (photoreceptors) in the retina that provide sharp central vision and color vision. Also see RODS.

Conjunctiva. The thin, moist tissue (membrane) that lines the inner surfaces of the eyelids and the outer surface of the sclera.

Contrast Sensitivity. The ability to perceive differences between an object and its background.

Cornea. The outer, transparent, dome-like structure that covers the iris, pupil, and anterior chamber; part of eye's focusing system.

Dilation. A process by which the pupil is temporarily enlarged with special eye drops (mydriatic); allows the eye care specialist to better view the inside of the eye.

Drusen. Tiny yellow or white deposits in the retina or optic nerve head.

Fovea. The central part of the macula that provides the sharpest vision.

Fundus. The interior lining of the eyeball, including the retina, optic disc, and macula; portion of the inner eye that can be seen during an eye examination by looking through the pupil.

Intraocular Pressure (IOP). Pressure of the fluid inside the eye; normal IOP varies among individuals.

Iris. The colored ring of tissue suspended behind the cornea and immediately in front of the lens; regulates the amount of light entering the eye by adjusting the size of the pupil.

Lens. The transparent, double convex (outward curve on both sides) structure suspended between the aqueous and vitreous; helps to focus light on the retina.

Macula. The small, sensitive area of the central retina; provides vision for fine work and reading.

Optic Cup. The white, cup-like area in the center of the optic disc.

Optic Disc/Optic Nerve Head. The circular area (disc) where the optic nerve connects to the retina.

Optic Nerve. The bundle of over one million nerve fibers that carry visual messages from the retina to the brain.

Peripheral Vison. Side vision; ability to see objects and movement outside of the direct line of vision.

Posterior Chamber. The space between the back of the iris and the front face of the vitreous; filled with aqueous fluid.

Pupil. The adjustable opening at the center of the iris that allows varying amounts of light to enter the eye.

Refraction. A test to determine the best eyeglasses or contact lenses to correct a refractive error (myopia, hyperopia, or astigmatism).

Retina. The light-sensitive layer of tissue that lines the back of the eyeball; sends visual messages through the optic nerve to the brain.

Retinal Pigment Epithelium (RPE). The pigment cell layer that nourishes the retinal cells; located just outside the retina and attached to the choroid.

Rods, Rod Cells. One type of specialized light-sensitive cells (photoreceptors) in the retina that provide side vision and the ability to see objects in dim light (night vision). Also see Cones.

Schlemm's Canal. The passageway for the aqueous fluid to leave the eye.

Sclera. The tough, white, outer layer (coat) of the eyeball; with the cornea, it protects the entire eyeball.

Tonometry. The standard to determine the fluid pressure inside the eye (intraocular pressure).

Trabecular Meshwork. The spongy, mesh-like tissue near the front of the eye that allows the aqueous fluid (humor) to flow to Schlemm's canal then out of the eye through ocular veins.

Uvea, Uveal Tract. The middle coat of the eyeball, consisting of the choroid in the back of the eye and the ciliary body and iris in the front of the eye.

Visual Acuity. The ability to distinguish details and shapes of objects; also called central vision.

Visual Field. The entire area that can be seen when the eye is forward, including peripheral vision.

Vitreous. The transparent, colorless mass of gel that lies behind lens and in front of retina.

Zonules. The fibers that hold the lens suspended in position and enable it to change shape during accommodation.

Zonular Apparatus. A three-dimensional system of fibers which originate close to the ciliary epithelium and pass forward in close association with the ciliary processes before fanning out to the lens capsule; it also helps maintain the hyaloid membrane.

Invention in General

The subject eye of the invention is an eye, either in its natural state or in a pretreated condition and may be the eye of any mammal, e.g., cat, dog, pig, horse, but is preferably a human eye. The information provided here, such as temperature and pressure, are for a human eye and could be adapted based on the disclosure to other animals. Possible pretreatments include removal of the epithelium, reduction of the intraocular pressure, application of an enzyme or other softening agent, and application of an anesthetic as well as suitable antiseptics including antibiotics and/or antivirals. It should be noted that some chemical agents can change the contraction temperature, so the therapeutic temperature in such cases must be appropriately adjusted. Other pretreatments include other refractive procedures, such as RK, PRK, and LASIK, assuming sufficient time for wound healing has elapsed. Also, pretreatment may include the application of a lubricant or sealant before applying the thermal energy.

Current treatments for presbyopia include glasses, contact lenses and surgery. Glasses and contact lenses are often considered a daily inconvenience. According to the tenet's of Tschernig, nearly 100 years ago, loss of zonular tension due to growth of the human lens is the major cause of presbyopia. This has been supported by recent surgical innovations of Schachar in which surgical implants are placed in scleral pocket incisions to stretch the sclera and reverse presbyopia. Such surgical correction is frequently unsuccessful or only marginally successful because it has a high level of morbidity and undesirable negative side-effects. The side-effects of surgical implants and other forms of traditional invasive surgical procedures include conjunctival scarring with inadequate tear film, implant dislocation with a loss of clinical effect, scleral perforation with or without vitreous loss, subconjunctival hemorrhaging which can cause cosmetic disfigurement for several weeks or longer, elevated intraocular pressure spike postoperatively, infection risk attendant to incision within the protective wall of the sclera, often requires an hour of surgical procedure time per eye, and leaves the sclera weakened. Other methods, such as surgical incisions or laser therapies, to effect an increase in zonular tension have similar marginal effectiveness and undesirable levels of morbidity, scleral weakening and bulging, and scarring, with a risk of permanent alteration of the delicate tear film. The present invention avoids these negative side-effects altogether, and requires no incision into the sclera.

The inventors have discovered a method and apparatus for treating presbyopia by taking advantage of the ability of a human eye to sustain damage to certain target tissues, such as, for example, peripheral lens cells, without such damage progressing to substantially adversely affecting non-target tissues. However, the eye is a notoriously delicate structure. Damage to the outer parts of the eye, such as, the outer sclera is undesirable because it presents a risk of pain, thinning, or even perforation from necrosis. Damage to the inner parts of the eye, such as the central lens is undesirable because it presents a risk of cataract formation, central capsule tear, or even phacolytic glaucoma if lens contents leak into the eye. As such, medical treatments and devices to treat the eye must be as precise as possible in order to achieve the desired result and to reduce the risk of injury and infection as a consequence of the medical treatment. According to the invention, a method and apparatus has been discovered which uses energy, preferably a specific mode of ultrasound, more preferably called high intensity focused ultrasound ("HIFU"), to safely and effectively treat presbyopia by applying energy to a desired target(s) in order to heat the target(s) to a particular temperature while greatly minimizing the collateral damage to adjacent tissues.

Because of the delicate nature of the eye, it is known that the eye does not tolerate generalized heating well. As such, one aspect of the novelty of the method and apparatus is the ability to treat an eye according to the invention without substantially adversely affecting the quality of vision. Another aspect of the novelty of the invention is the ability to direct the eye structures to preferentially heal and physiologically change, and improve the quality of vision. For example, the present invention provides a method and apparatus to safely heat zonule fibers, causing contraction of the zonules; such contraction increases the accommodative amplitude in the eye and as such, near vision is improved in the presbyope. More generalized heating would be associated with undesirable side effects such as risk of uveitis (inflammation within the eye), and cataract formation.

The inventive method permits therapeutic, effective heating of specific targeted eye tissues without the common undesirable side-effects associated with applying heat to sensitive structures. It is preferred that the methods of the invention utilize ultrasonic waves. It is more preferred that the method employ high intensity focused ultrasound ("HIFU") to treat the target tissues. As such, it is preferred that the apparatus of the invention emit ultrasonic waves; and it is more preferred that the apparatus be a high intensity focused ultrasound device to heat the target eye tissues. The inventors have found that a HIFU device can create a localized thermal injury in a desired target tissue area without damaging the surrounding tissues. In a preferred embodiment, HIFU can cause thermal injury to the eye non-invasively and in discrete targeted locations within the eye, preferably to a circumferential plane along the lens equator, outside the central lens.

HIFU is a promising field for minimal or non-invasive therapy. Generally, HIFU has been used in two kinds of applications: 1) the destruction of small identifiable sites, and 2) the de-bulking of tumors. As such, HIFU is commonly associated with generalized heating and disablement of discrete target tissues which can be targeted below even an opaque tissue surface. The method of the present invention is novel in that HIFU is applied to target tissues where preservation of the structure and function of the target tissues is desired. The method is novel in that the structure and function of the target tissues are improved following HIFU treatment. The HIFU pulse results in a discrete rice kernal shaped pulse of about 1 mm×250 $\mu$m zone of heating per pulse.

The use of high intensity focused ultrasound for therapeutic purposes results from the discovery that it is possible to heat desired tissue targets within the eye while sustaining insignificant damage outside the target region. The present invention is novel in being the first to describe the use of HIFU to treat eye disorders, such as, for example, presbyopia. A method and apparatus for non-invasively treating presbyopia is achieved by inducing a highly localized thermal injury to a target area, with the target area having a length of about 1 mm.

Depending on the target area, the thermal injury can achieve various effects. The inventors have discovered a method in which a thermal injury can increase, directly or indirectly, tension of the zonules and thereby increase accommodative amplitude. Further, the inventors have discovered a method in which a thermal injury can slow or suspend the growth rate of the lens. Also, the inventors have discovered a method in which a thermal injury can permanently stop or retard the stretching and/or the growth of the lens. Conventional A or B scan ultrasonography lacks the necessary precision to discretely affect target tissues and precisely elevate temperature over time without collateral damage. Generalized damage within a structure as small as the eye results in risk of glaucoma, cataract, uveitis, corneal edema and scarring, among other conditions.

Figure 1:
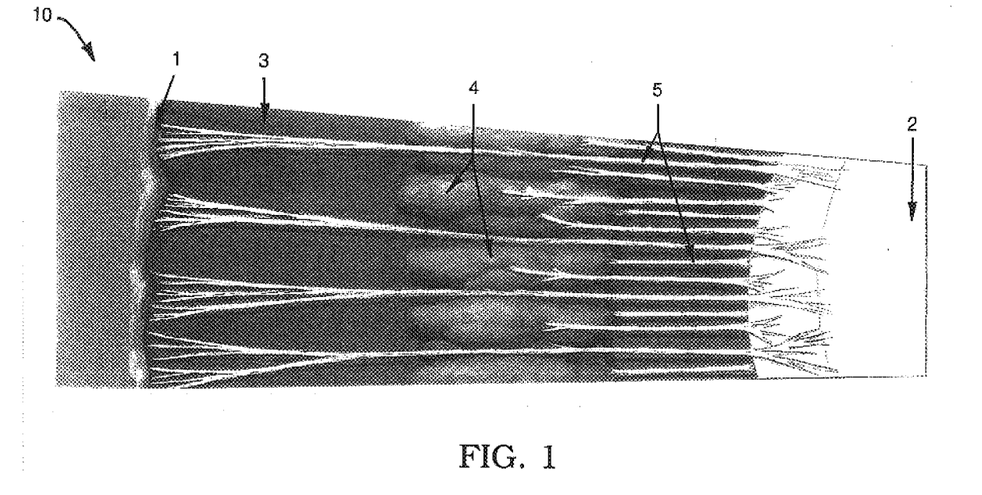
FIG. 1 is a schematic view of a portion of an eye showing the area between the lens and the retina.
Figure 2:
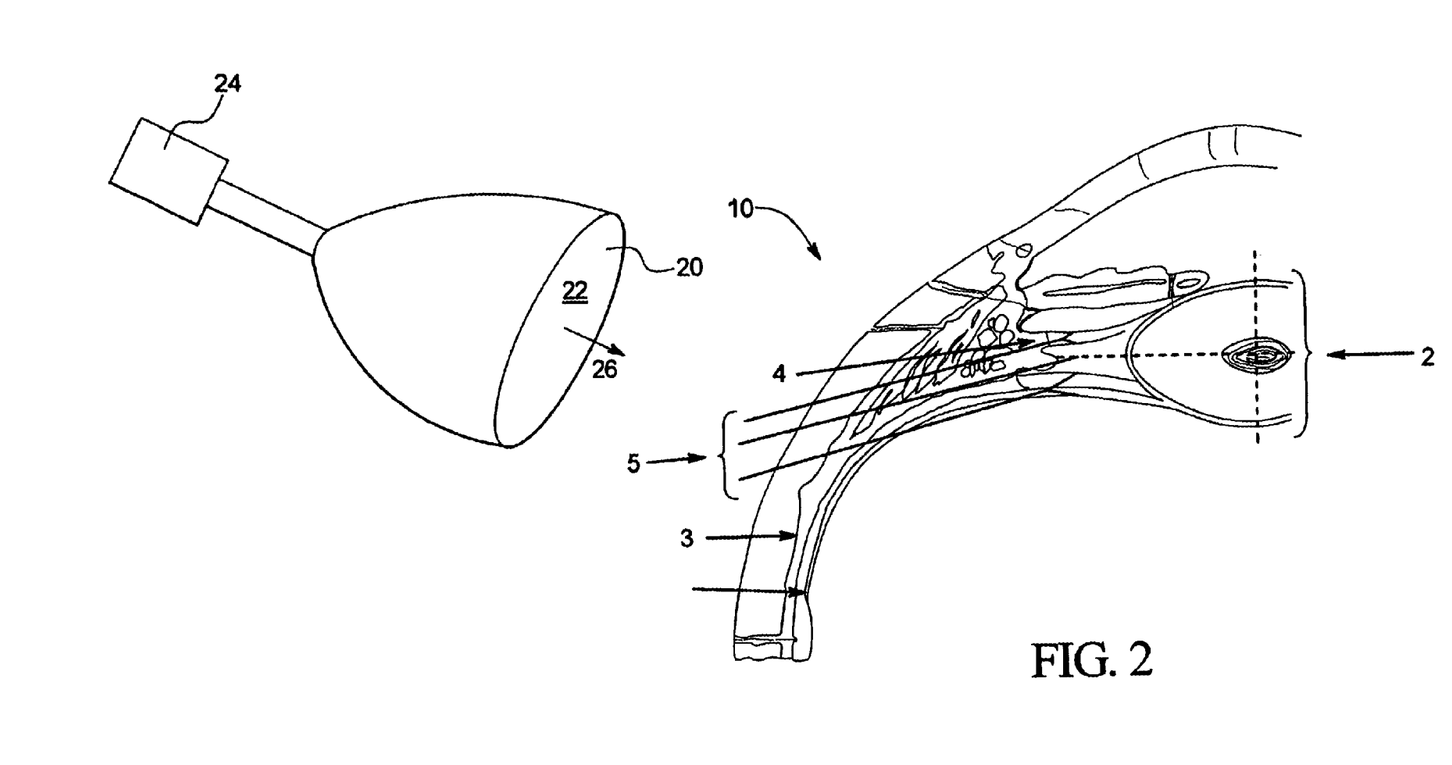
FIG. 2 is a cross-sectional schematic view of a portion of the eye showing various components or organelles of the eye.

The invention involves directing HIFU to a specific area or areas of the eye. Referring to FIG. 1, the energy can be focused at any point which would allow for treatment of the eye 10, such as treatment of presbyopia, for example, from the ora serrata 1 to the lens 2. The HIFU may be focused on any of the orbiculus ciliaris 3, ciliary processes 4, zonular fibers 5, or lens 2. The energy may be focused on a ciliary muscle at any point or area from the or serrata 1 to the lens 2. Alternatively, or in addition, the HIFU may be focused on the zonular fibers 5 (stretching among structures including, but not limited to, the ora serrata 1, the orbiculus ciliaris 3 of the ciliary body covered by the ciliary part of the retina, and the ciliary processes with zonules ultimately fanning out at 6 and blending into the lens capsule 2) where the zone includes ciliary epithelium through peripheral zonules. Alternatively, or in addition, the HIFU may be focused on an area which spans from the peripheral lens capsule and peripheral lens cellular architecture (including, but not limited to, the lens capsule, lens cortex, and lens nucleus). As shown in FIG. 2, the depth of each area where the HIFU may be directed gradually progresses toward the center of the eye 10. It is to be understood that the target areas and organelles on the eye are guidelines to illustrate and provide direction and orientation of some specific point as well as the areas that are to receive HIFU treatment. Each area shares common space with its preceding and succeeding area. As such, a structure may exist in more than one area. Furthermore, it is possible to further divide any of the areas into additional areas.

Figure 3:
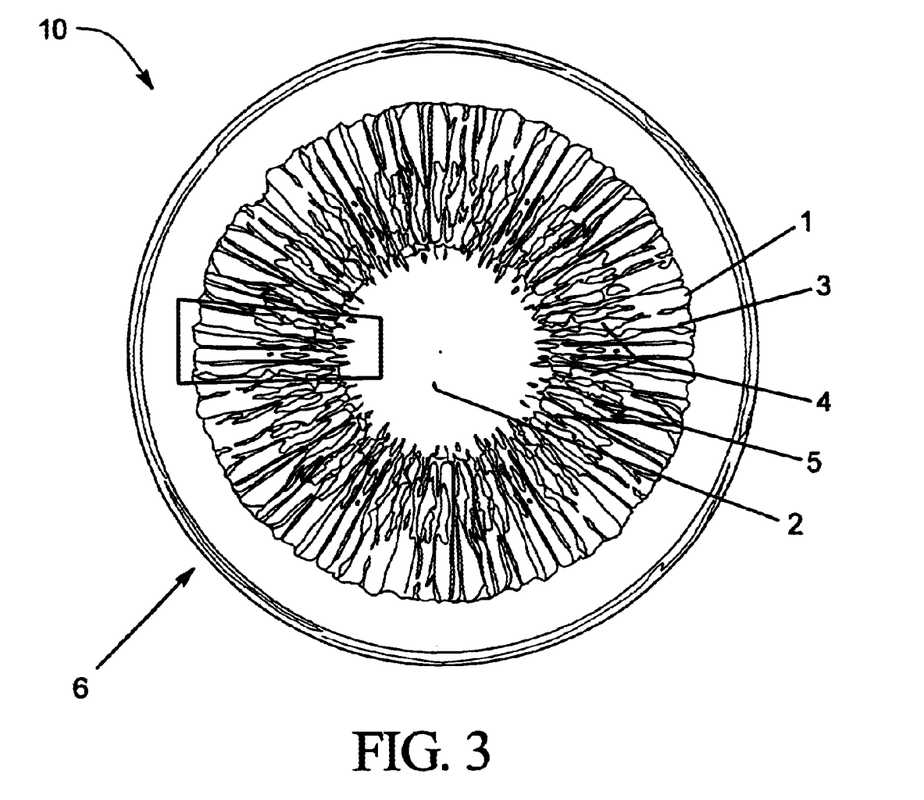
FIG. 3 is a schematic front view of an eye.

Referring to FIG. 3 along with FIGS. 1 and 2 the relationship of the organelles in the eye 10 and their relative positions can be appreciated. In short, areas in FIG. 3 between the sclera 6 and lens 2 can be subjected to the focused energy of an HIFU beam. Depending on the degree of presbyopia being suffered by the patient the beam of HIFU may be directed at a single point or a plurality of different points—on a single organelle or a plurality of different organelles.

The subject eye can receive a single HIFU treatment or a plurality of treatments at different points in time in accordance with the methods and apparatus described. Further, during each treatment session or time of exposure to HIFU, a zone or treatment region can receive a HIFU treatment singularly or in combination with other zones, in a serial or parallel fashion. Treatment of multiple target areas or zones can produce an additive effect in restoring accommodative amplitude in the presbyopic eye. Treatment can also be applied circumferentially or in a serial fashion such that treatment can be repeated along the same depth to produce cumulative effects over time. Treatment may also be applied along different depths in the plane of the lens equator (in any area from sclera 6 to the lens 2) which will also create additive effects in the improvement of accommodative amplitude. Multiple treatments may be applied in one session or in separate sessions. When in separate sessions, the time between discrete sessions may range from a very short time interval, such as, for example, microseconds, to sessions that are separated by days, months or even years.

Thermal injury, fibrosis or secondary contraction of tissues including, but not limited to, the equatorial lens capsule, the zonular apparatus, ciliary epithelium, the longitudinal muscle or the sclera are useful therapies which are uniquely achieved using the present invention noninvasively to improve the condition of eye disorders such as presbyopia. Improvement depends on the degree of control and the ability to control and localize treatment to the eye structures. The present invention can simultaneously retard lens diameter growth and tighten the zonular apparatus. This accomplishment contributes to the treatment of presbyopia in several ways. According to the invention, the methods can delay the onset of the disorder, reduce its rate of advancement, and simultaneously restore accommodative amplitude.

Other conditions, such as glaucoma and or ocular hypertension, in which increased outflow of fluid from the eye is desired, can be effected by alteration in mechanical filtration achieved by adjacent thermal injury to angle structures such as the trabecular meshwork located just anterior to the ciliary body.

According to the present invention, a non-incisional treatment method is preferred, especially where energy is applied to the eye through the conjunctiva and scleral wall. Variables such as a scatter of energy, an alteration in the path of transmitted energy, or an alteration in the configuration of a treatment may be considered when practicing the invention. For example, the curvature of the sclera may be taken into consideration because it can focus an acoustic wavefront. As such, ultrasonic energy with acoustic modulation of the incident energy can be employed to create a highly localized and predictable and accurate point of treatment in the eye. A treatment in which a probe providing four simultaneous applications is used could easily treat the circumference of the eye using pulses of about 1 to 2 seconds duration in less than five minutes. The probe could be designed to optimize its focal distance using a separate A-scan ultrasonic component.

A method of the present invention comprises the use of HIFU to obtain localized contraction of the zonules. The zonules may be contracted indirectly by focusing the treatment methods to an outer area near the sclera 6 or lens 2. Also, the zonules may be contracted directly by focusing the treatment method directly on or near the zonular fiber 5. It is well known that denaturation of protein results in change in its three dimensional structure and a shortening of the component comprised of the protein. Heating of zonules to obtain a change in the structural integrity, but short of the temperature at which coagulative necrosis is reached can accomplish such contraction or shortening. Temperature required varies with pulse duration, but should be on the order of 50° to 70° C.; and more generally under 100° C. and above 45° C. Such thermal contraction is induced by applying HIFU energy through the walls of the eye, preferably along a plane parallel to the posterior iris and about 2.5 mm posterior to the limbus. This energy may also be applied about 1.5 mm posterior to the limbus, or about 0.3 to 6 mm, and preferably about 1 to 6 mm. As such, the application of energy, which preferentially heats and contracts zonules in the equatorial region, may be applied circumferentially or performed at discrete cardinal points, symmetrically placed.

The zonules, which are comprised of fibrillin, may be contracted when an application of thermal energy causes the fibrillin to change its structural integrity, i.e. soften or "melt". Temperatures between about 45° C. and 100° C., when applied for an appropriate length of time, result in contraction of the zonules. Pulse durations on the order of 1 to 2 seconds are preferred, though a range of milliseconds to under 10 seconds could achieve desired clinical results. Even shorter pulses, particularly when on the order of 1 khz or greater, can be used to achieve a pseudo-continuous effect. There are many radially oriented zonules that connect from a band anterior to posterior to the lens equator. Each zonule is connected to a ciliary process, which is part of the ciliary body and located about 2.5 mm posterior to the iris root. It is a preferred to heat and contract equatorial zonules, though anterior and posterior zonules may also be contracted and supply a therapeutic effect.

Zonules are an effective target for HIFU because of their connection to the lens capsule. When zonules are heated using a HIFU transducer, contraction of the zonules can occur. Zonule contraction increases the tension of the zonular apparatus. Increased zonular tension plays a direct role in an increase in the degree of accommodative amplitude the lens is able to achieve when focusing on near objects.

It would however not be obvious to one skilled in the art of ophthalmology nor the use of ultrasound to use the noninvasive methods of the present invention, as achieving discrete heating of specific zones within the eye and through the walls of the eye, while avoiding damage to adjacent structures such as the central lens, cornea and outer sclera because until the development of the present invention, ophthalmologic HIFU has been limited to ablation of lesions on or near the retina.

Increased accommodative amplitude resulting from restoration of zonular resting tension as a result of contraction of tissues in the areas described above using references to FIGS. 1, 2 and 3 correlates with a higher quality of near vision and thus a reduction in the detrimental effects of presbyopia. Focusing HIFU on multiple points on different areas and/or on different organelles of the eye can potentially create an additive effect, which is not possible with surgical intervention other than by weakening the outer sclera as close to the full circumference as increased morbidity that results will allow. In addition, treatment of the lens 2 or areas thereabout affects the increase in lens diameter, and by limiting this increase retards and may in fact prophylactically prevent the progression of presbyopia.

In order to combat the effects of presbyopia, HIFU treatment according to the present invention is effective among structures including but not limited to the lens equator, extending from the peripheral lens cells, through the zonules, the ciliary muscles and the inner sclera. In a preferred embodiment, HIFU is directed towards the lens equator and the energy is above approximately 0.5 MHz focused within the lens equatorial plane at variable controlled distances. This can cause contraction and inducing a desired thermal injury to structures, such as, peripheral lens cells. For example, treatment of the ciliary processes 4 or the area near such will result in a decrease of inflow of aqueous fluid, allowing effective treatment of glaucoma and or ocular hypertension.

In practicing the invention, ultrasonic energy may be directed to peripheral lens cells so that the progression of accommodative decline resulting from presbyopia can be suspended or stopped altogether. The inventors have discovered a method of using HIFU to alter the elasticity of the lens capsule and slow lens cell growth. According to the present invention, it is possible to induce sufficient growth resistance of the lens capsule by damaging peripheral lens cells such that presbyopia can be prevented.

The present invention provides highly localized treatment, while the outer sclera, central lens, and anterior segment vasculature are protected. As such, the invention provides a method and apparatus to treat presbyopia without increasing the external diameter of the sclera or otherwise creating lesions in, weakening, or incising the external sclera. Treatment on or around the sclera 6 will alter the inner half of sclera by causing some scarring and thinning with subsequent pull on the zonular apparatus to which the inner sclera and ciliary muscle are in proximity. Scleral bulge is unnecessary, and the effectiveness of applying HIFU energy to treatment in the area is due, in part, to contraction of the small portion of ciliary longitudinal muscle located adjacent to the sclera. As a result, significantly less scleral weakness occurs than through available surgical methods and the outer scleral diameter remains, for the most part, unchanged.

A hallmark of the invention is the restoration of accommodative amplitude by heating target tissue to induce a physiological change while non-target tissues receive a sufficiently low energy density to create a clinically insignificant increase in temperature. By limiting treatment to approximately a band of thickness of about 1 mm along the plane of the lens equator, the risk of phthisis is minimized because not all tissues are heated. As such, risks, such as, for example, ischemia of the anterior segment, are minimized because most of the ciliary vasculature is not compromised during the heating methods.

A preferred embodiment of the invention induces thermal injury within a region localized to about 1 mm radially along the line of treatment, using a HIFU device with three separate probes to achieve the various depths relative to outer sclera at which such injury is desired. In this preferred embodiment, each pulse produces an area of heat extending inward approximately about 1 mm from the beginning of the treatment point and having measurements of about 250 microns in width and depth with minimal temperature elevation outside this treatment region. Surrounding tissues maintain a relatively normal body temperature level.

In a preferred embodiment, the entire circumference may be treated along each of the three target tissue depths, with each pulse of energy lasting about 1 to 2 seconds, and each receiving a different number of pulses depending on which zone depth is treated. Outer treatment zone 1 ranges from about 300 microns to 1.3 mm internal to the outer sclera; as such it generally receives about 200 pulses maximum over an average 18 mm diameter at the lens equator. Intermediate zone 2 ranges from about 1.5 to 2.5 mm internal to the outer sclera; as such, it receives about 150 pulses maximum. Inner zone 3 ranges from about 2.7 to 6.0 mm internal to the outer sclera; and, as such, it receives about 100 pulses maximum.

The present invention may achieve an increase accommodative amplitude by about 2 to 12 diopters. Factors that influence the amount of accommodation restored include the amount of circumference area treated, the duration and gradient of heat applied to the target tissues, the accuracy of heat effecting the target tissues, and the modulus of elasticity of the target tissues. The method and apparatus of the present invention can be repeated for additional effect as needed.

All or any of the areas or zones of treatment depth can achieve increased accommodative effect in the eye. To simplify treatment, the probes can have several transducers connected along a radius of curvature, allowing simultaneous treatment at about four locations per quadrant with a reduction in the maximum treatment to about 50 applications of energy lasting approximately 1 to 2 seconds, or less than about 2 minutes total per eye to achieve a 200 pulse treatment; which can be repeated for each of the three depths of treatment. Three different depths can easily be treated around the circumference of the eye in less than about 10 minutes per eye, regardless of whether a single depth is treated, or any combination of the three depths is selected. However, variables such as the age of the patient, the amount of accommodation which must be restored, and any history of prior treatment may affect the duration of treatment. While a preferred embodiment includes a water bath in a HIFU application, a waveguide or probe can be used for reflection of ultrasonic energy, and thus deliver the energy via a direct probe contact to the eye.

Changing the state or conformation (e.g. "melting") any protein, including fibrillin of which the zonules are composed, and which is present in lens capsule along with collagen causes contraction and restoration of accommodative amplitude as well.

Collagen contraction typically occurs at an elevated temperature, at about 57° C., and preferably at about 90 to 100° C., for about 2 seconds, depending on the amount of heat applied and the duration of its application. Lower levels of heat can create thermal injury with contraction of tissue. This heat can be applied continuously or in a pulsed fashion. A preferred embodiment exposes the external sclera to temperatures sufficiently above 50° C. in order to invoke protein denaturation. The sclera has been shown to tolerate temperatures of 50° C. for several seconds without any clinically significant injury. The melting point of most proteins is below 67° C. Until the development of the present invention, the therapeutic practice of heating proteins has been largely restricted to collagen contraction methodology or coagulative necrosis with generalized tissue lysis and destruction.

The methods and apparatus of the present invention are not limited to the treatment of presbyopia. Other embodiments of the invention include treating disorders such as, for example, glaucoma or ocular hypertension by altering the stretch of tissue along the Canal of Schlemm where aqueous fluid is drained. This therapy may alleviate the detrimental effects of such disorders by contracting the inner sclera or longitudinal ciliary muscle by inducing a localized thermal injury to the eye, without altering exposed sclera and without increasing the diameter of the sclera.

Another embodiment may encompass visualization of structures including, but not limited to, the lens equator, the ciliary wall, zonules or lens equator plane via an "A" scan or a "B" scan. A and B scans are well known to ophthalmologists, where an A scan provides a linear beam allowing distance measurement, and a B scan provides scanning ultrasound suitable for imaging. A quality image of the structures may be obtained by firing a test pulse of energy that non-invasively localizes the structure to provide a two dimensional scan wherein the ultrasonic energy can be effected by the temperature gradient. For example, conventional ultrasonic energy allows for image-guided treatment to identify the correct plane of treatment, and further may include driving a low intensity pulse or pulses to achieve two-dimensional imaging within that plane for more specific localization of treatment. It is an object of an embodiment of the present invention to analyze the acoustic waves where incident ultrasonic energy results in greatest absorption and to modify the treatment beam using principles of ultrasonic thermo-therapy. Adjustments and repeat testing may be exercised, as needed, and a higher intensity ultrasonic energy source may be employed to alter the temperature gradient.

HIFU treatment circumferentially or at discrete cardinal points around the eye increases the percentage of contracted zonules and its clinical effect. A treatment sphere of just under 2 mm diameter would allow near complete circumferential treatment in 16 discrete applications. Each treatment region may use very short treatment times of under 30 seconds for slower heating or preferably about 2 seconds for more rapid heating and better localization per application. Pulsed heating, and more rapid heating limits thermal diffusion to surrounding tissue and thereby increases tissue localization.

A scan ultrasonography can be employed to measure changes in the subject eye, such as, for example, the degree of contraction resulting from HIFU treatment. Spikes representing the inner wall of the eye and lens equator can be followed in real-time during treatment, and changes in their distance can be detected and measured. As such, the information can be used to modify the treatment during it application to the eye. Two-dimensional, non-invasive temperature data can be scanned by using a real-time high-speed displacement-tracking algorithm resulting from processing beamformed RF-data from commercially available ultrasonic scanners. As such, the treatment point can be localized and the quality of focused ultrasound can be assessed before zonular contraction or contraction of any area or organelle of the eye is effected.

HIFU devices having transducers positioned with or without phased arrays, can effect highly localized heating at a distance from the surface of conjunctiva and sclera through which the energy is focused. Such an embodiment allows detection and localization of such treatment by first allowing identification of the key structures of the zonular apparatus—the lens equator, a space of about 2.5 mm where the zonules connect to the lens equator as well as anterior and posterior to the equator, and the ciliary processes with their connection to the ciliary body and scleral wall on the external side. The dimensions of the treatment region will vary largely proportionally to the length of the eye, and or the diameter of the cornea.

Phased arrays can reduce energy loss or loss of focus that otherwise can occur by scatter and dispersion of energy focus as the wave travels through biological tissue. This has been shown in the treatment of tumors below the skin surface using ultrasonic phased arrays, known as ultrasonic thermo-therapy, and similarly via induction of potentially therapeutic lesions limited to the AV node of the heart for treatment of arrhythmias of the node from externally placed ultrasonic phased arrays.

In a preferred embodiment, test firing a low intensity pulse with localization within the treatment plane of a slight temperature gradient induced at the point of focus allows for more specific localization of the treatment; for example, the center of the treatment focus can be about 2.0 mm from the lens equator. This allows for a treatment area of about a 0.5 mm radius sphere with a core temperature gradient of about 90 to 100° C., provided there is a rapid drop off in the gradient beyond the region of focus. Outside the focal region the temperature gradient drops rapidly such that structures such as the sclera and lens capsule gradient is preferably less than about 47° C., where cell death is known to occur.

In order to safely contract eye tissues, such as, for example, the zonular apparatus or to reduce the rate of lens expansion by damaging peripheral lens cells, the apparatus of the present invention requires precise localization of treatment, so that preferential heating of the target tissues can be selected without substantially adversely heating and damaging the outer sclera or the central part of the lens of the eye. A preferred embodiment of the apparatus is a HIFU transducer because focused ultrasonic energy is capable of destroying sub-surface tissue without substantially harming the overlying tissues. More particularly, applied at a reduced wattage, a thermal injury can be controlled to below the level of coagulative necrosis, which typically occurs at 90 to 100° C. At a reduced wattage, lesions may be carefully created which can cause both immediate and delayed disruption of the target tissue.

The HIFU transducer of the present invention utilizes a ceramic, piezoelectric crystal to focus ultrasonic energy on discrete regions within the eye without damaging the external eye or delicate structures surrounding the point of focus. By using a saucer-shaped, ceramic, pieo-electric source (i.e., a transducer) having a diameter of about 8.4 cm, a radius of curvature at about 15 cm, operating at about 1.7 MHz and 100 to 300 watts, sub-surface tissue can be destroyed and/or modified without harming the overlying tissue. HIFU at lower energy settings can heat tissue above 50° C., but below 90 to 100° C. where coagulative necrosis may occur. As shown in FIG. 2, the transducer 20 includes a ceramic piezoelectric source 22. When energized by an energy source 24, the transducer 20 can apply HIFU energy 26 to a discrete regoin within the eye 10 without damaging nearby structures, thus effectively preventing and/or treating presbyopia as previously discussed.

Treatment may be employed using a single, or preferably multiple, HIFU transducers, each being about 4 mm above the sclera and focused approximately along the lens equator at about 1.5 mm posterior to the limbus. The transducers according to the present invention may treat several target tissue areas with one application of HIFU energy. For example, four to five target tissue areas may be identified to receive HIFU energy and upon exposure to the HIFU energy, each area can simultaneously receive the energy. Either a phased array or separate probes for specific distances may be used to direct treatment to any one or to any combination of the target tissue zones.

These and other objects, advantages, and features of the invention will become apparent to those persons skilled in the art upon reading the details of the present invention as more fully described below.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular method, treatment, device, situation, material, composition of matter, process, process step or steps, to the objective, spirit and scope of the present invention. All such modifications are intended to be within the scope of the claims appended hereto.

That which is claimed is:

1. A method of treating an eye, comprising the steps of:
   identifying an area of an eye;
   focusing a device capable of directing high intensity focused ultrasound (HIFU) energy on the area;
   generating HIFU energy from the device onto the area;
   wherein the energy transfer from the device to the area results in an increase in temperature of the area; and
   repeating the identifying focusing and generating a plurality of times on areas of the eye which result in contracting thereby resulting in treating presbyopia wherein the repeating creates an additive effect, and wherein the energy is provided circumferentially on each area.

2. The method of claim 1, wherein energy transfer results in contracting the area.

3. The method of claim 2, wherein the contracting increases tension on a component of the eye in connection with a lens of the eye.

4. The method of claim 2, wherein the contracting increases tension on a component of the eye in an amount sufficient to treat presbyopia.

5. The method of claim 4, wherein the component of the eye is selected from the group consisting of a ciliary muscle, a zonule, and a peripheral lens capsule.

6. The method of claim 2, wherein the contracting occurs to a peripheral lens capsule and secondarily increases tension of zonules of the eye.

7. The method of claim 1, wherein the area is on a component of the eye selected from the group consisting of inner scleral tissue, longitudinal ciliary muscle tissue and ciliary epithelium.

8. The method of claim 1, wherein the area is on a component of the eye selected from the group consisting of zonular fibers and peripheral zonules.

9. The method of claim 1, wherein the area is on a component of the eye selected from the group consisting of peripheral lens capsule tissue and peripheral lens cellular architecture.

10. The method of claim 1, wherein said repeating is continued in a manner so as to result in contracting a distance of about 50 microns or more.

11. The method of claim 10, wherein said contracting is about 100 microns or more.

12. The method of claim 11, wherein said contracting is about 200 microns or more.

13. The method of claim 12, wherein said contracting is about 300 microns or more.

14. The method of claim 1, wherein the energy results in slowing lens diameter growth.

15. The method of claim 1, wherein the energy transfer alters the modulus of elasticity of a lens capsule of the eye.

16. The method of claim 1, wherein the area has no dimension larger than 2 millimeters.

17. The method of claim 1, wherein the area has no dimension larger than 1 millimeter.

18. The method of claim 1, wherein the HIFU energy increases the temperature of the area to a temperature in a range from about 47° C. to about 100° C.

19. The method of claim 1, wherein the HIFU energy increases the temperature of the area to a temperature in a range from about 47° C. to about 80° C.

20. The method of claim 1, wherein the HIFU energy increases the temperature of the area to a temperature in a range from about 60° C. to about 70° C.

21. The method of claim 1, wherein said identifying step comprises applying ultrasound scanning imaging to identify the area.

22. The method of claim 1, wherein said generating is in a pulse having a duration of two seconds or less.

23. A method of treating an eye, comprising the steps of:
identifying an area of an eye;
focusing a device capable of directing high intensity focused ultrasound (HIFU) energy on the area;
generating HIFU energy from the device onto the area;
wherein the energy transfer from the device to the area results in an increase in temperature of the area; and
repeating the identifying, focusing and generating a plurality of times on areas of the eye which result in contracting thereby resulting in treating presbyopia wherein the repeating is continued in a manner so as to result in contracting a distance of about 50 microns or more.

24. The method of claim 23, wherein the energy transfer results in contracting the area.

25. The method of claim 24, wherein the contracting increases tension on a component of the eye in connection with a lens of the eye.

26. The method of claim 24, wherein the contracting increases tension on a component of the eye in an amount sufficient to treat presbyopia.

27. The method of claim 26, wherein the component of the eye is selected from the group consisting of a ciliary muscle, a zonule, and a perpheral lens capsule.

28. The method of claim 24, wherein the contracting occurs to a peripheral lens capsule and secondarily increases tension of zonules of the eye.

29. The method of claim 23, wherein said contracting is about 100 microns or more.

30. The method of claim 29, wherein said contracting is about 200 microns or more.

31. The method of claim 30, wherein said contracting is about 300 microns or more.

32. A method of treating an eye, comprising the steps of:
identifying an area of an eye;
focusing a device capable of directing high intensity focused ultrasound (HIFU) energy on the area;
generating HIFU energy from the device onto the area;
wherein the energy transfer from the device to the area results in an increase in temperature of the area, and wherein the generating is in a pulse having a duration of two seconds or less.

33. The method of claim 32, wherein the energy transfer results in contracting the area.

34. The method of claim 33, wherein the contracting increases tension on a component of the eye in connection with a lens of the eye.

35. The method of claim 33, wherein the contracting increases tension on a component of the eye in an amount sufficient to treat presbyopia.

36. The method of claim 35, wherein the component of the eye is selected from the group conditioning of a ciliary muscle, a zonule, and a peripheral lens capsule.

* * * * *